United States Patent [19]

Aiken

[11] Patent Number: 4,531,530

[45] Date of Patent: Jul. 30, 1985

[54] DENTAL FLOSS HOLDER

[76] Inventor: Ormarion J. Aiken, Box 305, Sandpoint, Id. 83864

[21] Appl. No.: 531,735

[22] Filed: Sep. 13, 1983

[51] Int. Cl.³ .............................................. A61C 15/00
[52] U.S. Cl. ........................................ 132/91; 132/93
[58] Field of Search ................... 132/89, 90, 91, 92 R, 132/92 A, 93

[56] References Cited

U.S. PATENT DOCUMENTS

| | | | |
|---|---|---|---|
| 3,892,249 | 7/1975 | Jones et al. | 132/89 |
| 4,002,183 | 1/1977 | Restall | 132/91 |
| 4,013,085 | 3/1977 | Wright | 132/89 |
| 4,460,002 | 7/1984 | Burdette, Jr. | 132/91 |

Primary Examiner—Hugh R. Chamblee
Assistant Examiner—Carolyn A. Harrison
Attorney, Agent, or Firm—Harvey Jacobson

[57] ABSTRACT

An elongated arched support member is provided including an elevated midportion an oppositely downwardly and endwise outwardly directed inclined end portions. A section of dental floss is provided and the lower ends of the end portions include structure which anchor opposite end portions of the section of dental floss relative thereto with said dental floss section in a tensioned state. The inner surfaces of the elongated member may engage and ride over the inner and outer side upper portions of adjacent teeth between which the section of floss is received as the arched member is oscillated lengthwise back and forth transversely of the associated gum ridge. The spacing between corresponding midportions of the floss support member and the floss section is at least generally equal to the vertical spacing between the crown surface of a tooth and the associated gum tissue. As the support member is oscillated back and forth, the inner surfaces of the inclined end portions thereof act as cam surfaces for upwardly displacing the support member, and thus the section of floss supported therefrom, at the end of each lengthwise stroke of the support member. In this manner, food debris as well as plaque may be scraped from between adjacent teeth.

2 Claims, 5 Drawing Figures

U.S. Patent   Jul. 30, 1985   4,531,530
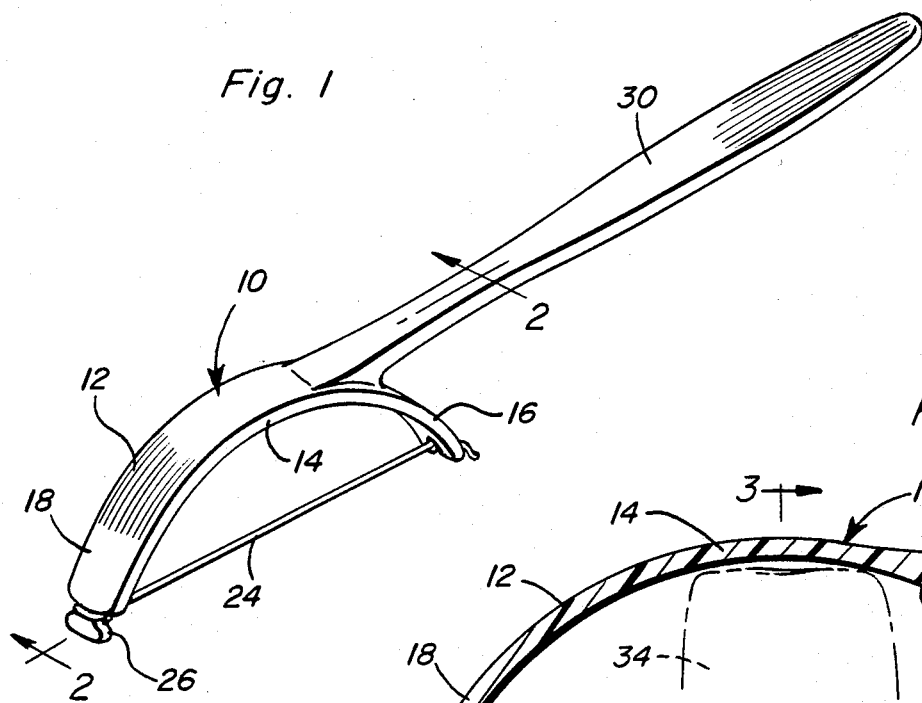
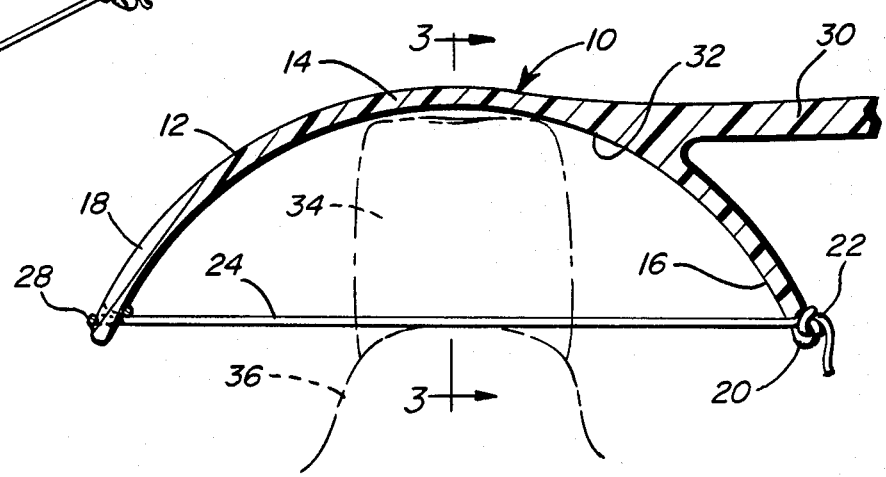
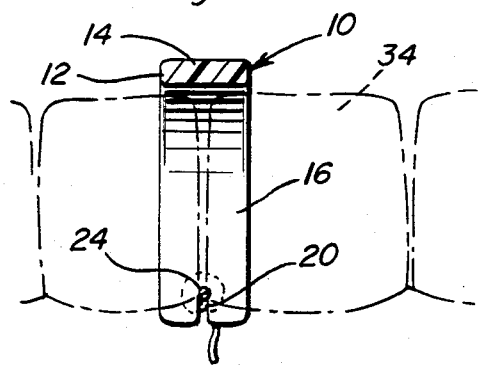
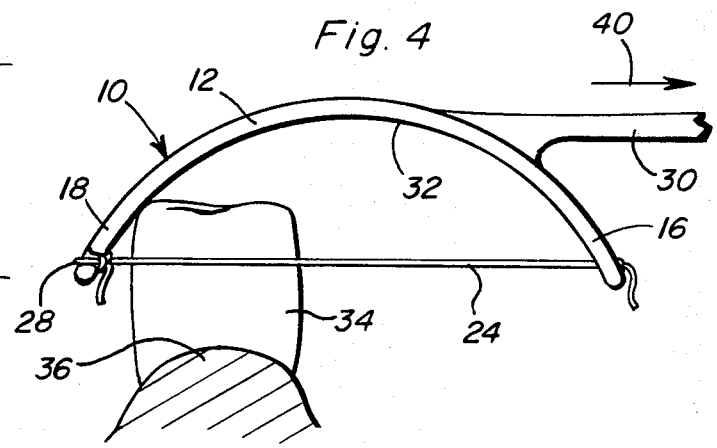
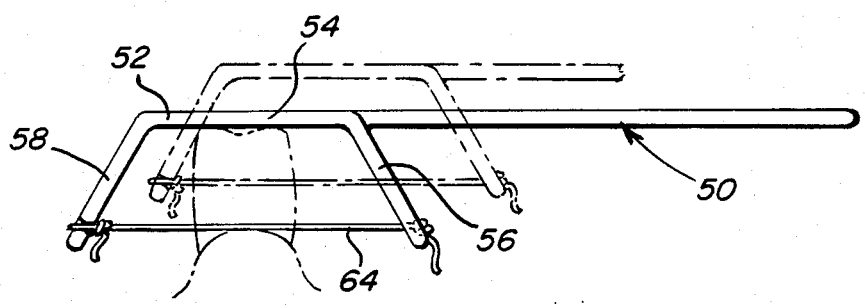

DENTAL FLOSS HOLDER

BACKGROUND OF THE INVENTION

In the recent past, it has become well known that dental hygiene may be greatly facilitated as a result of the proper "flossing" of teeth at least twice daily. However, when proper flossing is carried out either manually without the aid of a floss holder or with the aid of a floss holder adjacent abrasive surfaces of adjacent teeth as well as plaque surfaces thereon can effect a tearing or eroding action on a length of floss with the result that two or three movements of floss along adjacent surfaces of teeth is sufficient to sever the floss section being used. This involves not only wastage of a dental floss but requires the use of a new section of floss, and perhaps several more, before a flossing operation can be completed. If the flossing operation is being performed manually without the use of a holder or with the use of a holder, the flossing operation is greatly lengthened in duration as each new section of floss is prepared for use. Accordingly, a need exists for a dental floss holder which may automatically provide two longitudinally spaced wear zones thereof for engaging abrasive tooth and plaque surfaces. By providing two discrete areas of usage of a single length of floss, the "life" of that length of floss is at least doubled.

Examples of various different forms of floss holders including some of the general structural and operational features of the instant invention are disclosed in U.S. Pat. Nos. 380,739, 542,782, 728,121, 918,281, 2,443,415, 4,002,183 and 4,051,857.

BRIEF DESCRIPTION OF THE INVENTION

The dental floss holder of the instant invention comprises an elongated arched floss holding member including an elevated midportion and oppositely downwardly and outwardly directed inclined end portions. In a first form of dental floss holder disclosed, the holder is constructed so as to include a substantially constant radius of curvature, but in a second form of floss holder the arched portion thereof includes a substantially straight midportion and oppositely and outwardly inclined and substantially straight opposite end portions. Both disclosed forms of the dental floss holder are constructed in a manner whereby the holder need be only longitudinally reciprocated transversely of a gum ridge while either downward or upward pressure is applied to the holder. The inner surfaces of the holder, at least at the opposite ends thereof, include oppositely downwardly and outwardly inclined inner surfaces comprising cam surfaces which engage and ride upon the inner and outer crown portions of adjacent teeth between which the associated section of floss is received. When the crown portions of adjacent teeth are engaged by the inner surfaces of the midportion of the holder, the midportion of the length of floss supported from the holder is disposed at or below the gum line and as the holder is lengthwise displaced to shift either end thereof toward the area of adjacent teeth between which the floss is received, the inner surfaces of that end portion of the holder ride on the adjacent side crown portions of the teeth between which the floss extends. This causes the floss to move from the gum line toward the crown of the teeth in order to perform the correct flossing operation.

The main object of this invention is to provide a dental floss holder which will greatly facilitate proper flossing of teeth and thereby promote good dental hygiene.

Another object of this invention is to provide a dental floss holder constructed in a manner whereby each section of dental floss being used during a flossing operation will have its life expectancy at least doubled.

Still another object of this invention is to provide a dental floss holder which may be constructed of different sizes so as to perform proper flossing operations on teeth of varying lengths.

A final object of this invention to be specifically enumerated herein is to provide a dental floss holder in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a first form of dental floss holder constructed in accordance with the present invention;

FIG. 2 is an enlarged fragmentary vertical sectional view taken substantially upon the plane indicated by the section line 2—2 of FIG. 1;

FIG. 3 is a vertical transverse sectional view taken substantially upon the plane indicated by the section line 3—3 of FIG. 2;

FIG. 4 is a fragmentary side elevational view of the dental floss holder in operation during a tooth flossing operation; and FIG. 5 is a side elevational view of a second form of dental floss holder constructed in accordance with the present invention.

DETAILED DESCRIPTION OF THE INVENTION

Referring now more specifically to the drawings, the numeral 10 generally designates a first form of dental floss hold constructed in accordance with the present invention. The holder 10 includes an elongated arched floss holding member 12 consisting of an elevated midportion 14 and downwardly curving opposite end portions 16 and 18. The end portion 16 is longitudinally slotted as at 20 for receiving the knotted end 22 of a section 24 of dental floss therethrough and the end portion 18 includes opposite side notches 26 whereby a looped end portion 28 of the section 24 may be anchored relative to the end portion 18. Further, the holding member 12 includes an elongated outwardly projecting integral handle 30 which projects tangentially outwardly from one end of the midportion 14.

In operation, the section 24 of dental floss is secured between the end portions 16 and 18 in a tensioned state, the end portions 16 and 18 being somewhat resilient, and the holder 10 is positioned with the section 24 received between adjacent teeth and the inner surface 32 of the holding member 12 abutted against the adjacent crown surfaces of the aforementioned adjacent teeth. The distance between the inner surface portion of the midportion 14 and the section 24 may be slightly greater than the height of a tooth from the crown to the adjacent gum area that when the inner surface of the midportion rests upon the crown of teeth 34 in the manner illustrated in FIG. 2 of the drawings drawings, the section 24 will be disposed at or below the adjacent gum tissue 36. Then, the handle 30 of the holder 10 is reciprocated back and forth while applying lateral pressure to maintain the inner surface 32 of the holding member 12 in contact with the adjacent teeth crowns. As the handle 30 is shifted in the direction of the arrow 40 in FIG. 4 from the position thereof illustrated in FIG. 2, the section 24 is displaced lengthwise and upwardly between the adjacent teeth 34. Then, as the handle 30 is shifted in a direction opposite to the arrow 40 in FIG. 4, the section 24 is shifted to the left and in a downward direction until the section 24 reaches or moves below the gum tissue 36 as the inner surface of the midportion 14 moves into contact with the top of the adjacent teeth 34. Then, further movement of the holder 10 to the left causes the inner surface of the end portion 16 to ride upwardly over the opposing upper crown surface portions of the adjacent teeth 34 and the section 24 to again ride upwardly between the adjacent teeth 34. Accordingly, with alternating horizontal lateral pressure applied to the handle 30, the adjacent sides of the adjacent teeth 34 may be properly flossed with a minimum of effort. Further, inasmuch as the section 24 is being longitudinally displaced as it is being raised or lowered along the adjacent sides of the adjacent teeth 34, wear upon the section 24 is distributed throughout substantially the entire length thereof with the result that the section 24 may be used for considerably longer periods of time before being severed by rough adjacent tooth or plaque surfaces.

With attention now invited more specifically to FIG. 5 of the drawings, a modified form of dental floss holder is referred to in general by the reference numeral 50. The holder 50 is generally structurally similar to the holder 10 in that it includes a holding member 52 corresponding to the holding member 12 and consisting of an upper midportion 54 and oppositely downwardly and outwardly inclined end portions 56 and 58 between whose lower ends a section 64 of dental floss is supported. The main difference between the holders 10 and 50 is that the end portions 56 and 58 of the holder 50 are inclined, but are longitudinally straight whereas the end portions 16 and 18 are curved and coextensive with the curved midportion 14 of the holder 10. However, the inner surfaces of the holding members 12 and 52 are of substantially the same mirror image contour on opposite sides of a plane disposed normal to the corresponding floss section and centrally intermediate the lower ends of the corresponding holding member, see FIGS. 4 and 5.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. The method of effecting proper flossing of teeth comprising mounting an elongated section of dental floss between the free ends of an arched support member with said section in a tensioned state and with said support member including an inner surface having a generally horizontal midportion and oppositely and outwardly directed opposite end portions, and longitudinally displacing said arched support member transversely of a gum ridge while said section of floss is disposed between two adjacent teeth projecting upwardly from said gum ridge and the inner surface of said arched support member rides in contact with the opposing crown surfaces of said adjacent teeth, whereby said inner surface and crown surfaces of said adjacent teeth will coact as guide surfaces and laterally displace said arched support member and floss section toward and away from said gum ridge at a predetermined rate and through a predetermined lateral distance as said arched support member is displaced back and forth across said crown surfaces.

2. A dental floss holder including an elongated arched floss holding member including an elevated midportion and oppositely downwardly and outwardly directed end portions, an elongated section of dental floss, the lower ends of said end portions including means anchoring opposite end portions of said section of dental flows relative thereto with said section in a tensioned state, the inner surfaces of said elongated member being of substantially the same mirror image contour on opposite sides of a plane disposed normal to said floss and centrally intermediate said lower ends and adapted to engage and ride over the inner and outer side upper portions of adjacent teeth between which said section of floss is received as said arched member is oscillated lengthwise back and forth across the associated gum ridge portion, the vertical spacing between the mid-portion of said floss section and the longitudinal mid-portion of the inner surfaces of said arched holding member being slightly greater than the height of a tooth from the crown to the adjacent gum area, whereby as said arched holding member is oscillated lengthwise back and forth with the inner surfaces thereof guidingly engaged with the crown portions of adjacent teeth between which the section of floss is received the floss section will be laterally displaced toward and away from the gum line at a predetermined rate and through a predetermined lateral distance.

* * * * *